US011550385B2

(12) United States Patent
Marcolino Quintao Severgnini et al.

(10) Patent No.: US 11,550,385 B2
(45) Date of Patent: Jan. 10, 2023

(54) DYNAMICALLY DEFORMABLE SURFACES TO ANALYZE USER CONDITIONS USING BIODATA

(71) Applicant: Toyota Motor Engineering & Manufacturing North America, Inc., Plano, TX (US)

(72) Inventors: Frederico Marcolino Quintao Severgnini, Ann Arbor, MI (US); Ercan Mehmet Dede, Ann Arbor, MI (US)

(73) Assignee: Toyota Motor Engineering & Manufacturing North America, Inc., Plano, TX (US)

( * ) Notice: Subject to any disclaimer, the term of this patent is extended or adjusted under 35 U.S.C. 154(b) by 739 days.

(21) Appl. No.: 16/526,047

(22) Filed: Jul. 30, 2019

(65) Prior Publication Data

US 2021/0031711 A1 Feb. 4, 2021

(51) Int. Cl.
*G06F 3/01* (2006.01)
*A61B 5/00* (2006.01)
(Continued)

(52) U.S. Cl.
CPC .................. *G06F 3/01* (2013.01); *A61B 5/00* (2013.01); *A61B 5/4266* (2013.01); *G06F 3/041* (2013.01);
(Continued)

(58) Field of Classification Search
CPC .......... G05B 13/00; G08B 6/00; G08B 23/00; G06F 3/0416; G06F 3/0482;
(Continued)

(56) References Cited

U.S. PATENT DOCUMENTS 9,092,093 B2 7/2015 Jubner et al.
9,128,525 B2 9/2015 Yair et al.
(Continued)

OTHER PUBLICATIONS

NPL Search (Apr. 23, 2022).*
(Continued)

*Primary Examiner* — Van T Trieu
(74) *Attorney, Agent, or Firm* — Christopher G. Darrow; Darrow Mustafa PC

(57) ABSTRACT

A surface of a vehicle component can be dynamically deformable surface. The dynamically deformable surface can be configured to undergo deformations to dynamically form a dynamic button or other user interface element on demand. The dynamically deformable surface can include one or more biosensors. When a user engages the dynamic button with a portion of the body, the one or more biosensors can acquire user biodata. The user biodata can be used by the vehicle as input for various purposes. For instance, the vehicle can operate as a health-monitoring and/or comfort monitoring system. As a result of these arrangements, buttons and other user interface elements can appear and disappear depending on the need and/or application, providing a cleaner vehicle cockpit interface and greatly expanding the possibilities of where such buttons can be located at and how many things can be controlled by the driver using physical interfaces.

18 Claims, 6 Drawing Sheets

(51) Int. Cl.
*G06F 3/041* (2006.01)
*B60R 16/037* (2006.01)
*B60Q 9/00* (2006.01)
*A61B 5/0533* (2021.01)
*A61B 5/0205* (2006.01)
*A61B 5/145* (2006.01)
*A61B 5/021* (2006.01)

(52) U.S. Cl.
CPC ............. *A61B 5/021* (2013.01); *A61B 5/0205* (2013.01); *A61B 5/0533* (2013.01); *A61B 5/14532* (2013.01); *A61B 5/14546* (2013.01); *A61B 5/6893* (2013.01); *A61B 5/746* (2013.01); *B60Q 9/00* (2013.01); *B60R 16/037* (2013.01)

(58) Field of Classification Search
CPC ...... G06F 3/0488; G06F 3/04883; G06F 3/01; G06F 3/016; G06F 3/041; A61B 5/00; A61B 5/02; A61B 5/024; A61B 5/145; A61B 5/1445; A61B 5/7275; B60K 28/00; B60K 28/06; B60K 28/063
See application file for complete search history.

(56) References Cited

U.S. PATENT DOCUMENTS

| | | | |
|---|---|---|---|
| 9,720,501 B2 | 8/2017 | Ray et al. | |
| 9,875,625 B2 | 1/2018 | Khoshkava et al. | |
| 9,939,900 B2 | 4/2018 | Cruz-Hernandez et al. | |
| 2006/0020216 A1* | 1/2006 | Oishi | A61B 5/0285 600/500 |
| 2008/0114218 A1* | 5/2008 | Suyama | B60K 28/066 600/300 |
| 2008/0114495 A1* | 5/2008 | Suyama | B60H 1/00742 700/276 |
| 2010/0035665 A1 | 2/2010 | Munson | |
| 2011/0193787 A1 | 8/2011 | Morishige et al. | |
| 2016/0291862 A1* | 10/2016 | Yaron | G06F 3/04883 |
| 2018/0037113 A1* | 2/2018 | Kim | A61B 5/18 |
| 2018/0116605 A1* | 5/2018 | Newberry | A61B 5/0002 |

OTHER PUBLICATIONS

Harrison et al., "Providing Dynamically Changeable Physical Buttons on a Visual Display", CHI 2009, Apr. 4-9, 2009, Boston, MA (10 pages).
Jiang et al., "Actuators Based on Liquid Crystalline Elastomer Materials", Nanoscale, Jun. 21, 2013 (37 pages).
Camargo et al., "Batch fabrication of optical actuators using nanotube-elastomer composites towards refreshable Braille displays", Journal of Micromechanics and Microengineering, published Jun. 7, 2012 (11 pages).
Gao et al., "Fully integrated wearable sensor arrays for multiplexed in situ perspiration analysis", Nature, Jan. 28, 2016 (30 pages).
Torras et al., "Tactile device based on opto-mechanical actuation of liquidcrystal elastomers", Sensors and Actuators A 208 Jan. 18, 2014 (9 pages).
Ding et al., "Human-Machine Interfacing Enabled by Triboelectric Nanogenerators and Tribotronics", Advanced Material Technologies, 2019 (16 pages).
Lippenberger et al., "Photoresponsive liquid crystal elastomers as feedback controlled light-driven actuators—theory, real-time behavior, limitations", Physics Procedia 83, 2016 (9 pages).
Tsimeris et al., "User Created Tangible Controls Using ForceForm: a Dynamically Deformable Interactive Surface", UIST'13 Adjunct, Oct. 6-9, 2013, St. Andrews, United Kingdom (3 pages).
Kweon et al., "Wearable high-performance pressure sensors based on three-dimensional electrospun conductive nanofibers", NPG Asia Materials, 2018 (12 pages).
Wang et al., "Soft Ultrathin Electronics Innervated Adaptive Fully Soft Robots", Advanced Materials, Feb. 5, 2018 (9 pages).

\* cited by examiner

DYNAMICALLY DEFORMABLE SURFACES TO ANALYZE USER CONDITIONS USING BIODATA

FIELD

The subject matter described herein relates in general to vehicles and, more particularly, to the interaction between vehicles and human occupants.

BACKGROUND

There are various in-vehicle user interfaces that enable a user to interact with a vehicle. For instance, a vehicle can be equipped with buttons, switches, and dials in various regions of cockpit, such as on the steering wheel, console, or doors. These user interfaces give users the ability to control certain vehicle functions. In some instances, the vehicle can be configured so that a driver or other vehicle occupant can more easily perceive the presence of user interface elements.

SUMMARY

In one respect, the present disclosure is directed to a system. The system includes a vehicle component. The system includes a dynamically deformable surface provided on the vehicle component. The dynamically deformable surface can be configured to deform in response to a stimulus. The system can include one or more biosensors. The one or more biosensors can be a part of the dynamically deformable surface. The system can include one or more processors. The one or more processors can be operatively connected to the dynamically deformable surface and to the one or more biosensors. The one or more processors can be configured to: cause the dynamically deformable surface to deform to form a dynamic button; and, responsive to the dynamic button being engaged by a body portion of the user, acquire user biodata using the one or more biosensors.

In another respect, the present disclosure is directed to a method. The method includes causing a dynamically deformable surface to deform to form a dynamic button. The dynamically deformable surface can be located on a vehicle component. The dynamically deformable surface can include one or more biosensors. The method can include, responsive to the dynamic button being engaged by a body portion of the user, acquiring, using the one or more biosensors, user biodata.

DETAILED DESCRIPTION

Figure 1:
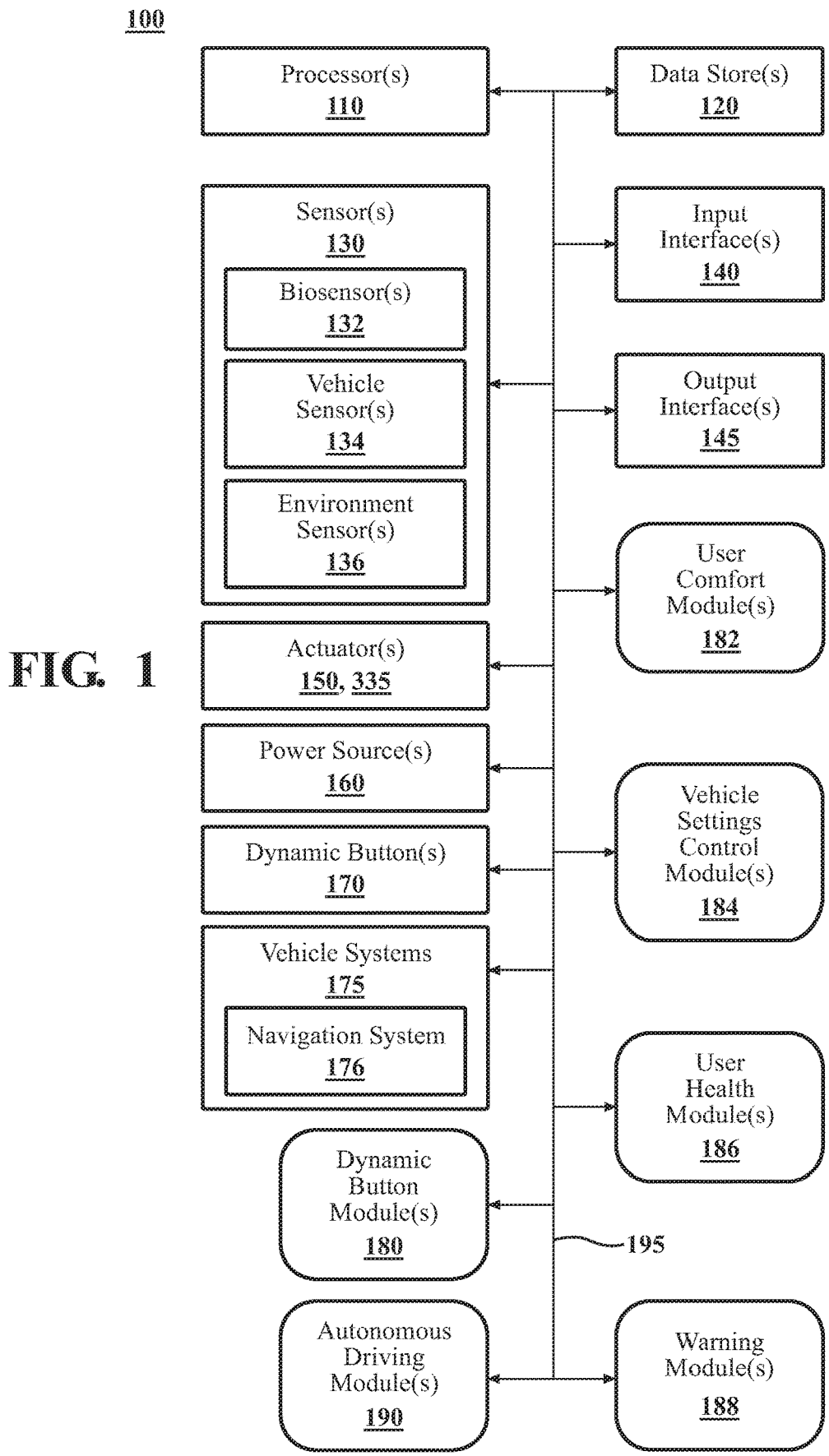
FIG. 1 is an example of a system for providing one or more dynamic buttons in a vehicle.

Physical buttons and other physical user interface elements within a vehicle remain fixed in a specific area. As a result, there is a limit of how many buttons or user interface elements can be added. Also, by adding too many buttons or user interface elements, the vehicle cockpit can become overly complicated, potentially making it confusing for the driver. According to arrangements described herein, one or more surfaces of a vehicle cockpit can be configured to undergo deformations to dynamically form a button or other user interface element on demand, depending on the need and/or application. By doing so, buttons and other user interface elements can appear and disappear. As a result, a cleaner cockpit interface can be achieved, while greatly expanding the possibilities of where such buttons can be located and how many things can be controlled by the driver using physical interfaces.

The button can include biosensors which can acquire data about one or more human parameters. Thus, when the button is engaged by a portion of a user's body, the biosensors can acquire user biodata. The user biodata can be used by the vehicle as input for various purposes. For instance, the vehicle can operate as a health-monitoring and/or comfort monitoring system. Such monitoring can be provided without creating an interface that is visually overwhelming.

Detailed embodiments are disclosed herein; however, it is to be understood that the disclosed embodiments are intended only as examples. Therefore, specific structural and functional details disclosed herein are not to be interpreted as limiting, but merely as a basis for the claims and as a representative basis for teaching one skilled in the art to variously employ the aspects herein in virtually any appropriately detailed structure. Further, the terms and phrases used herein are not intended to be limiting but rather to provide an understandable description of possible implementations. Various embodiments are shown in FIGS. 1-6, but the embodiments are not limited to the illustrated structure or application.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details.

Arrangements described herein can be used in connection with a vehicle. As used herein, "vehicle" means any form of motorized transport. In one or more implementations, the vehicle can be an automobile. While arrangements will be described herein with respect to automobiles, it will be understood that embodiments are not limited to automobiles. In some implementations, the vehicle may be a watercraft, an aircraft or any other form of motorized transport. Additional aspects of the vehicle will be shown and described later in this description.

Referring to FIG. 1, an example of a system 100 for providing one or more dynamic buttons in a vehicle is shown. The dynamic buttons can acquire user biodata, which can be analyzed to assess user conditions (e.g., health, comfort, etc.) and to determine appropriate actions or suggested actions based on the user conditions.

The system 100 can include various elements. Some of the possible elements of the system 100 are shown in FIG. 1 and will now be described. However, it will be understood that it is not necessary for the system 100 to have all of the elements shown in FIG. 1 or described herein. The system 100 can have any combination of the various elements shown in FIG. 1. Further, the system 100 can have additional elements to those shown in FIG. 1. In some arrangements, the system 100 may not include one or more of the elements shown in FIG. 1. Further, while the various elements may be shown and/or described as being located on or within a vehicle, it will be understood that one or more of these elements can be located external to the vehicle. Thus, such elements are not located on, within, or otherwise carried by the vehicle. Further, the elements shown may be physically separated by large distances. Indeed, one or more of the elements can be located remote from the vehicle.

The system 100 can include one or more processors 110, one or more data stores 120, one or more sensors 130, one or more input interfaces 140, one or more output interfaces 145, one or more actuators 150, one or more power sources 160, and one or more dynamic buttons 170, one or more vehicle systems 175, and/or one or more modules (e.g., dynamic button module(s) 180, user comfort module(s) 182, vehicle settings control module(s) 184, user health module(s) 186, warning module(s) 188, and/or autonomous driving module(s) 190). Each of these elements will be described in turn below.

The system 100 can include one or more processors 110. "Processor" means any component or group of components that are configured to execute any of the processes described herein or any form of instructions to carry out such processes or cause such processes to be performed. The processor(s) 110 may be implemented with one or more general-purpose and/or one or more special-purpose processors. Examples of suitable processors include microprocessors, microcontrollers, DSP processors, and other circuitry that can execute software. Further examples of suitable processors include, but are not limited to, a central processing unit (CPU), an array processor, a vector processor, a digital signal processor (DSP), a field-programmable gate array (FPGA), a programmable logic array (PLA), an application specific integrated circuit (ASIC), programmable logic circuitry, and a controller. The processor(s) 110 can include at least one hardware circuit (e.g., an integrated circuit) configured to carry out instructions contained in program code. In arrangements in which there is a plurality of processors 110, such processors can work independently from each other or one or more processors can work in combination with each other.

The system 100 can include one or more data stores 120 for storing one or more types of data. The data store(s) 120 can include volatile and/or non-volatile memory. Examples of suitable data stores 120 include RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The data store(s) 120 can be a component of the processor(s) 110, or the data store(s) 120 can be operatively connected to the processor(s) 110 for use thereby.

The data store(s) 120 can store any suitable data or information in any form, now known or later developed. For instance, the data store(s) 120 can store information about any of the elements of the system 100.

In one or more arrangements, the data store(s) 120 can store health-related data (e.g., symptoms, diagnoses, treatment, etc.). The health-related data may be general health-related data and/or health-related data with respect to a particular user. In one or more arrangements, the data store(s) 120 can store health thresholds, profiles, and/or preferences. In one or more arrangements, the data store(s) 120 can store user contact information, including medical provider information, payment information, pharmacy information, medication information. In one or more arrangements, the data store(s) 120 can store user biodata acquired by one or more elements of the system 100. In one or more arrangements, the data store(s) 120 can store user comfort settings and data related to human comfort, generally or specific to a particular user.

The system 100 can include one or more sensors 130. "Sensor" means any device, component and/or system that can detect, determine, assess, monitor, measure, quantify and/or sense something. The one or more sensors 130 can detect, determine, assess, monitor, measure, quantify and/or sense in real-time. As used herein, the term "real-time" means a level of processing responsiveness that a user, entity, component, and/or system senses as sufficiently immediate for a particular process or determination to be made, or that enables a processor to process data at substantially the same rate as some external process or faster.

In arrangements in which there are a plurality of sensors 130, the sensors 130 can work independently from each other. Alternatively, two or more of the sensors 130 can work in combination with each other. In such case, the two or more sensors 130 can form a sensor network. The sensor(s) 130 can be operatively connected to the processor(s) 110, the data store(s) 120, and/or other element of the system 100 (including any of the elements shown in FIG. 1). The sensor(s) 130 can acquire data of at least a portion of the system 100.

The sensor(s) 130 can include one or more biosensors 132. The biosensor(s) 132 can be configured to acquire biodata of a user (i.e., a human being). Biodata includes any biological data, biomarkers, and/or physiological data that can be analyzed to determine a state or condition of a user, such as a comfort level or a health condition. Non-limiting examples of the biodata can include sweat glucose (to monitor blood sugar), blood pressure, galvanic skin response (to measure degrees of arousal), sodium and potassium (to measure dehydration), among others. In some arrangements, the biosensor(s) 132 can be configured to acquire biodata by direct contact with a body portion of a human being, such as a portion of a human's hand, finger, or thumb.

In some arrangements, the sensor(s) 130 can include one or more vehicle sensors 134. The vehicle sensor(s) 134 can detect, determine, assess, monitor, measure, quantify and/or sense information about the vehicle itself. Examples of such data can include position, orientation, speed, settings, performance of the vehicle systems 175 or components thereof, etc. Further examples include cabin temperature, seat pressure, and cabin air quality.

The sensor(s) 130 can include one or more environment sensors 136 configured to detect, determine, assess, monitor, measure, quantify, acquire, and/or sense driving environment data. "Driving environment data" includes any data or information about the external environment in which a vehicle is located or one or more portions thereof. In one or more arrangements, the environment sensors 136 can include one or more cameras, one or more radar sensors, one or more lidar sensors, one or more sonar sensors, and/or one or more ranging sensors.

The system 100 can include one or more input interfaces 140. An "input interface" includes any device, component, system, element or arrangement or groups thereof that enable information/data to be entered into a machine. The input interface(s) 140 can receive an input from a user (e.g., a person) or other entity. Any suitable input interface(s) 140 can be used, including, for example, a keypad, display, touch screen, multi-touch screen, button, joystick, mouse, trackball, microphone, gesture recognition (radar, lidar, camera, or ultrasound-based), and/or combinations thereof.

The system 100 can include one or more output interfaces 145. An "output interface" includes any device, component, system, element or arrangement or groups thereof that enable information/data to be presented to a user (e.g., a person) or other entity. The output interface(s) 145 can present information/data to a user or other entity. The output interface(s) 145 can include a display, an earphone, haptic device, and/or speaker. Some components of the system 100 may serve as both a component of the input interface(s) 140 and a component of the output interface(s) 145.

The system 100 can include one or more actuators 150. The actuator(s) 150 can be used at various locations in the vehicle. The actuator(s) 150 can modify, adjust and/or alter one or more of the vehicle systems 175 or components thereof. The actuator(s) 150 can perform such actions responsive to receiving signals or other inputs from the processor(s) 110, module(s), and/or other element(s) of the system 100. The actuator(s) can include motors, pneumatic actuators, hydraulic pistons, relays, solenoids, and/or piezoelectric actuators, just to name a few possibilities.

Figure 3A:
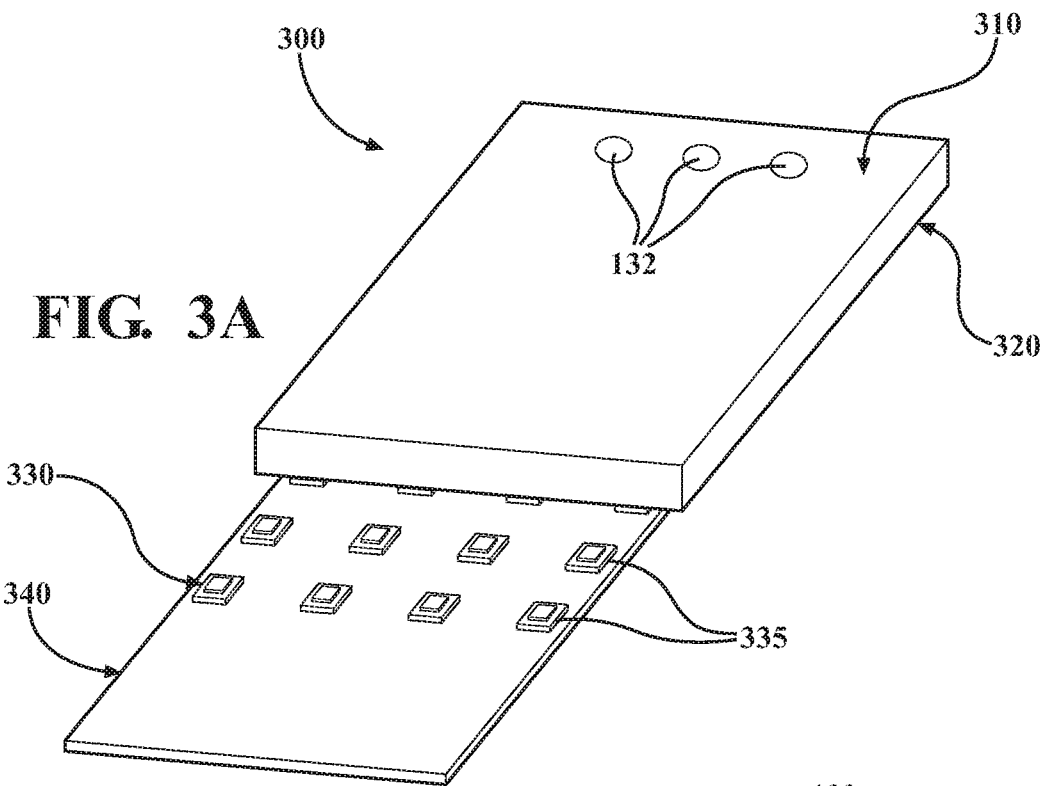
FIG. 3A shows an example of a dynamically deformable surface in a non-activated mode.
Figure 3B:
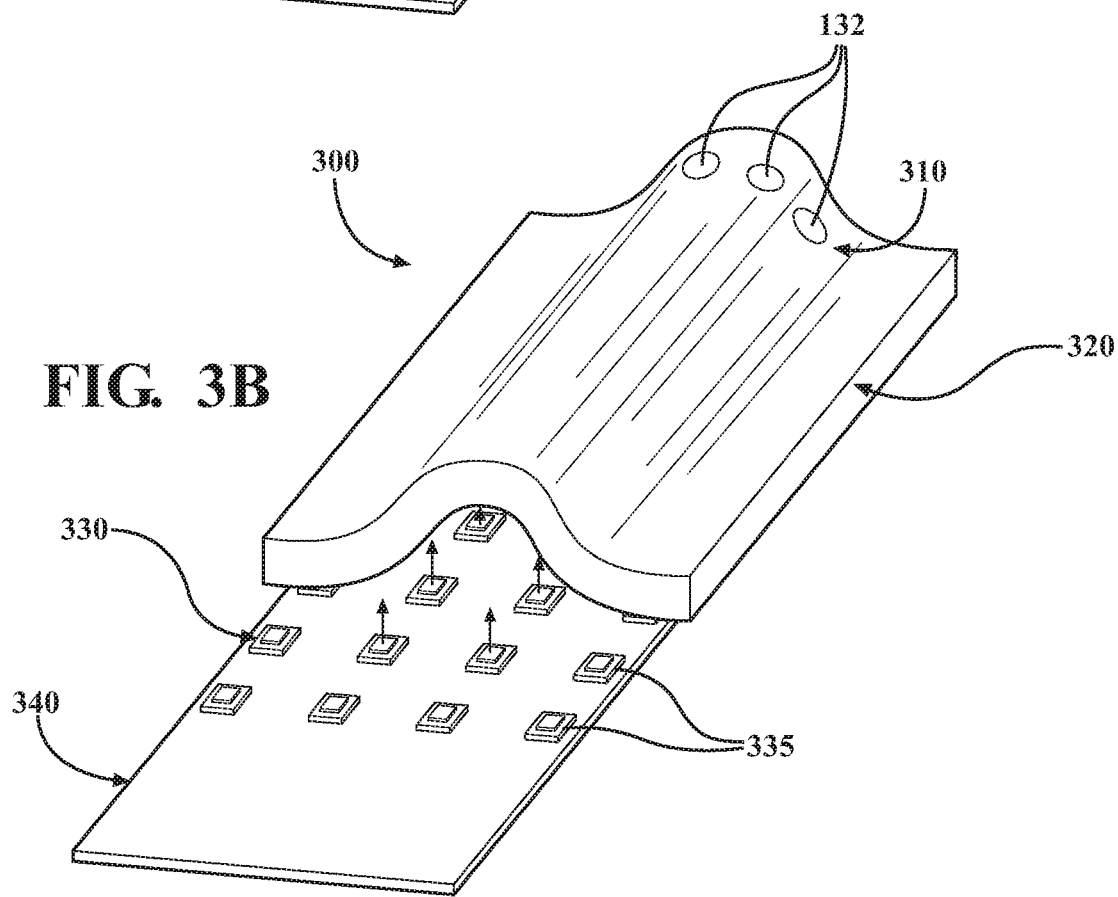
FIG. 3B shows an example of the dynamically deformable surface in an activated mode.

In some arrangements, the actuator(s) 150 can include one or more actuators 335 (see FIGS. 3A-3B). The actuators 335 can be used to activate a deformable surface to form the dynamic button(s) 170, as will be described herein. The actuator(s) 335 can include light sources, fluidic actuators, voltage sources, and/or thermal energy sources, just to name a few possibilities.

As noted above, the system 100 can include one or more power sources 160. The power source(s) 160 can be any power source capable of and/or configured to energize the actuators 150, 335 or other component(s) of the system 100 and/or vehicle. For example, the power source(s) 160 can include one or more batteries, one or more fuel cells, one or more generators (e.g. piezoelectric), one or more alternators, one or more solar cells, and combinations thereof.

The system 100 can include one or more dynamic buttons 170. The dynamic button(s) 170 can be any user interface element that can be engaged by a portion of a user's body and/or perceived by a user's sense of touch. The dynamic button(s) 170 can have any suitable size, shape, and/or configuration. In some arrangements, the dynamic button(s) 170 can be defined by a protrusion on a surface. In some arrangements, the dynamic button(s) 170 can be defined by a recess in a surface.

As will be described herein, the dynamic button 170 can be provided in any suitable location within the vehicle, and the location can be configured by a user or some other entity. As used herein, the dynamic button(s) 170 can be considered to be dynamic in that, when not activated, the dynamic button(s) 170 are not perceivable at least by a user's sense of sight and/or touch, but, when activated, becomes perceivable by a user at least to the sense of sight and/or touch. Additional details of the dynamic button(s) 170 will be described later in this specification.

The system 100 can include one or more vehicle systems 175. The one or more vehicle systems 175 can include a propulsion system, a braking system, a steering system, throttle system, a transmission system, a signaling system, and/or a navigation system 176. Each of these systems can include one or more mechanisms, devices, elements, components, systems, and/or combination thereof, now known or later developed. The above examples of the vehicle systems 175 are non-limiting. Indeed, it will be understood that the vehicle systems 175 can include more, fewer, or different vehicle systems. It should be appreciated that although particular vehicle systems are separately defined, each or any of the systems or portions thereof may be otherwise combined or segregated via hardware and/or software within the vehicle.

The navigation system 176 can include one or more mechanisms, devices, elements, components, systems, applications and/or combinations thereof, now known or later developed, configured to determine the geographic location of the vehicle and/or to determine a travel route for the vehicle. The navigation system 176 can include one or more mapping applications to determine a travel route for the vehicle. The navigation system 176 can include a global positioning system, a local positioning system, or a geolocation system.

There can be one or more vehicle setting associated with one or more of the vehicle systems 175 that can be user configuration. Examples of such vehicle settings can include cabin temperature, air conditioning temperature and/or output level, seat position, sound level, instrument panel brightness, just to name a few possibilities.

The system 100 can include one or more modules. The modules can be implemented as computer readable program code that, when executed by a processor, implement one or more of the various processes described herein. One or more of the modules can be a component of the processor(s) 110, or one or more of the modules can be executed on and/or distributed among other processing systems to which the processor(s) 110 is operatively connected. The modules can include instructions (e.g., program logic) executable by one or more processor(s) 110. Alternatively or in addition, one or more data stores 120 may contain such instructions. The modules described herein can include artificial or computational intelligence elements, e.g., neural network, fuzzy logic or other machine learning algorithms. Further, the modules can be distributed among a plurality of modules.

The system 100 can include one or more dynamic button modules 180. The dynamic button module(s) 180 can include profiles and logic for actively controlling a deformable surface within the vehicle to form the dynamic button(s) 170. The dynamic button module(s) 180 can be configured to send signals to a deformable surface.

The dynamic button module(s) 180 can be configured to determine when the dynamic button(s) 170 should be activated or deactivated. The dynamic button module(s) 180 can be configured to do so in any suitable manner. For instance, the dynamic button module(s) 180 can be configured to activate the dynamic button(s) 170 in response to detected user inputs (e.g., commands) provided on the input interface(s) 140. As an example, as user may provide a voice command or may press a user interface element (e.g., touch pad, button, etc.). Alternatively or in addition, the dynamic button module(s) 180 can be configured to activate the dynamic button(s) 170 in response to detecting certain conditions or situations. These conditions or situations may relate to the user, the vehicle, the user's operation of the vehicle, etc. The dynamic button module(s) 180 can be configured to detect these conditions or situations by analyzing data or information acquired by the sensor(s) 130. Still further, the dynamic button module(s) 180 can be configured to activate the dynamic button(s) 170 at a predetermined time, periodically, irregularly, randomly, or responsive to a condition, event, or input.

The dynamic button module(s) 180 can use profiles, parameters, and/or settings loaded into the dynamic button module(s) 180 and/or stored in the data store(s) 120. In addition to causing the dynamic button(s) 170 to appear and disappear, the dynamic button module(s) 180 can be configured to draw a user's attention to the dynamic button(s) 170. For instance, the dynamic button module(s) 180 can cause the dynamic button(s) 170 to be illuminated or have a different surface texture, stiffness, and/or color than the surrounding surface.

As used herein, "cause" or "causing" means to make, force, compel, direct, command, instruct, and/or enable an event or action to occur or at least be in a state where such event or action may occur, either in a direct or indirect manner. For instance, the dynamic button module(s) 180 can selectively permit or prevent the flow of electrical energy from the power source(s) 160 to the actuator(s) 150 or other actuators associated with a deformable surface. The dynamic button module(s) 180 can be configured to send control signals or commands over a communication network to the actuators 150.

As will be explained in greater detail below, the biosensor(s) 132 can be associated with the dynamic button(s) 170. Thus, when the dynamic button(s) 170 are activated, a user may engage the dynamic button(s) 170 with a portion of his or her body (e.g., hand, finger, thumb, etc.). When such contact occurs, the biosensor(s) 132 can begin to acquire and/or monitor user biodata.

The system 100 can include one or more user comfort modules 182. The user comfort module(s) 182 can include profiles and logic for determining a comfort level of a user. The user comfort module(s) 182 can be configured to do so in any suitable manner, such as by using any suitable techniques, now known or later developed. For instance, the user comfort module(s) 182 can be configured to analyze biodata acquired by the biosensor(s) 132. The user comfort module(s) 182 can retrieve raw data from the biosensor(s) 132 and/or from the data store(s) 120.

In some instances, the user comfort module(s) 182 can take into account other inputs, such as user inputs provided on the input interface(s) 140 and/or vehicle data acquired by the vehicle sensor(s) 134. For instance, user biodata coupled with the current vehicle cabin temperature may indicate that the user is uncomfortably hot or cold. In other arrangements, the user comfort module(s) 182 can determine whether a user is excited or aroused based on the user biodata. If the user comfort module(s) 182 determine that the user is comfortable, then the user comfort module(s) 182 may take no action.

The system 100 can include one or more vehicle settings control modules 184. The vehicle settings control module(s) 184 can include profiles and logic for actively controlling one or more vehicle systems 175 or portions thereof to facilitate user comfort. If the user comfort module(s) 182 determines that the user is not comfortable, then vehicle settings control module(s) 184 can be configured to determine which vehicle setting(s) should be adjusted to increase the user's comfort. For instance, if it is determined that the user is cold, the vehicle settings control module(s) 184 can determine that the cabin temperature settings of the vehicle climate control system should be increased. As another example, if it is determined that the user is agitated because the cabin is too noisy, the vehicle settings control module(s) 184 can determine that the audio volume should be decreased.

The vehicle settings control module(s) 184 can be configured to do so in any suitable manner. In some arrangements, the vehicle settings control module(s) 184 can automatically adjust the vehicle setting(s). In other arrangements, the vehicle settings control module(s) 184 can be configured to prompt the user as to whether he or she wants a vehicle setting to be adjusted. For instance, the vehicle settings control module(s) 184 can cause a prompt to be presented on the output interface(s) 145. The prompt can be visual, audial, and/or haptic.

The user can respond to the prompt via the input interface(s) 140. For instance, the user can tap a touchscreen, give a voice command, etc. The vehicle settings control module(s) 184 can analyze the user inputs to determine an appropriate action for adjusting a vehicle setting.

If the user input indicates that the user does not want the vehicle setting(s) to be adjusted, the vehicle settings control module(s) 184 may take no further action. If the user input indicates that the user wants the vehicle setting(s) to be adjusted, the vehicle settings control module(s) 184 can be configured to cause the vehicle setting(s) to be adjusted. For instance, the vehicle settings control module(s) 184 can be configured to cause one or more actuators 150 to be activated or deactivated. The vehicle settings control module(s) 184 can be configured send control signals or commands over a communication network to the actuator(s) 150.

The system 100 can include one or more user health modules 186. The user health module(s) 186 can include profiles and logic for determining a health condition of a user and/or classifying the urgency level of the health condition. The user health module(s) 186 can be configured to do so in any suitable manner. For instance, the user health module(s) 186 can be configured to analyze user biodata acquired by the biosensor(s) 132. In some instances, the user health module(s) 186 may take into account other inputs, such as user inputs provided on the input interface(s) 140. The user health module(s) 186 can retrieve raw data from the biosensor(s) 132 and/or from the data store(s) 120. The user health module(s) 186 can also retrieve medial data from any suitable data source.

The user health module(s) 186 can analyze the user biodata to detect a health condition. For instance, the user health module(s) 186 can compare the acquired user biodata to a library of health conditions to determine which health condition(s) the user may have and/or eliminate which health condition(s) the user does not have. Further, the user health module(s) 186 can compare the acquired user biodata to symptoms of various health conditions. The user health module(s) 186 can be configured to use big data to detect a health condition.

In some arrangements, the biodata can include glucose levels and/or blood pressure. The user health module(s) 186 can analyze the glucose levels and/or blood pressure to determine whether the user may have a health condition. In some arrangements, the biodata may include analytes in a user's sweat. The user health module(s) 186 can analyze the analytes to assess a user's drug treatment program and/or if the dosage is appropriate.

If no health condition is detected, the user health module(s) 186 may take no action. However, when a health condition is detected, the user health module(s) 186 can be configured to classify the urgency level of the health condition. In some arrangements, the user health module(s) 186 can determine the urgency level based on a predetermined urgency level associated with the particularly health condition. The urgency levels can be assigned by a user, a medical provider, a vehicle manufacturer, or some other entity.

Alternatively, the user health module(s) 186 can classify the urgency level of the detected health condition by comparing user biodata acquired by the biosensors(s) 132 and/or other data to one or more predetermined health thresholds (a predetermined number or range of numbers) associated with each level of urgency. When the biodata meets a predetermined health threshold(s), the user health module(s) 186 can be configured to present a warning or an alert and/or to cause a warning or an alert to be presented.

In one or more arrangements, various health conditions can be associated with an urgency level. Such associations can be set by user, vehicle manufacturer, health provider, or some other entity. There can be any suitable number of the urgency levels. In some arrangements, the urgency levels can include low, medium, and high. However, there can be more or fewer urgency levels. The user health module(s) 186 can be configured to send the detected health condition and/or urgency level to other modules or other portions of the system 100.

In one or more arrangements, the system 100 can include one or more warning modules 188. The warning module(s) 188 can be configured to cause a warning to be presented to the user if warranted based on the detected health condition.

In one or more arrangements described herein, the warning module(s) 188 can be configured to cause the output interface(s) 145 and/or other component of the system 100 to be activated to provide a warning. The warning can be any type of warning, including, for example, a visual warning, an audial warning, or a haptic warning. The content of the warning and/or the manner in which it is output to the user can vary depending on the urgency level of a detected health condition. Some examples of different warnings that can be provided will be described later.

When the vehicle is an autonomous vehicle, the system 100 can include one or more autonomous driving modules 190. The autonomous driving module(s) 190 can receive data from the sensor(s) 130 and/or any other type of system capable of capturing information relating to the vehicle and/or the external environment of the vehicle. The autonomous driving module(s) 190 can receive, capture, and/or determine location information for obstacles within the external environment of the vehicle for use by the processor(s) 110, and/or one or more of the modules described herein to estimate position and orientation of the vehicle, vehicle position in global coordinates based on signals from a plurality of satellites, or any other data and/or signals that could be used to determine the current state of the vehicle or determine the position of the vehicle in respect to its environment for use in either creating a map or determining the position of the vehicle in respect to map data. The autonomous driving module(s) 190 can determine and/or detect the presence of obstacles, the location of obstacles, the identity of obstacles, and/or other environmental features including traffic signs, trees, shrubs, neighboring vehicles, pedestrians, etc.

The autonomous driving module(s) 190 can determine travel path(s), current autonomous driving maneuvers for the vehicle, future autonomous driving maneuvers and/or modifications to current autonomous driving maneuvers based on data acquired by the sensor(s) 130, driving scene models, and/or data from any other suitable source. "Driving maneuver" means one or more actions that affect the movement of a vehicle. Examples of driving maneuvers include: accelerating, decelerating, braking, turning, moving in a lateral direction of the vehicle, changing travel lanes, merging into a travel lane, and/or reversing, just to name a few possibilities. The autonomous driving module(s) 190 can cause, directly or indirectly, such autonomous driving maneuvers to be implemented. The autonomous driving module(s) 190 can execute various vehicle functions and/or to transmit data to, receive data from, interact with, and/or control the vehicle or one or more systems thereof (e.g. one or more of vehicle systems 175).

The processor(s) 110 and/or the autonomous driving module(s) 190 can be operatively connected to communicate with the various vehicle systems 175 and/or individual components thereof. For example, the processor(s) 110 and/or the autonomous driving module(s) 190 can be in communication to send and/or receive information from the various vehicle systems 175 to control the movement, speed, maneuvering, heading, direction, etc. of the vehicle. The processor(s) 110 and/or the autonomous driving module(s) 190 may control some or all of these vehicle systems 175 and, thus, may be partially or fully autonomous.

For instance, when operating in an autonomous mode, the processor(s) 110 and/or the autonomous driving module(s) 190 can control the direction and/or speed of the vehicle. The processor(s) 110 and/or the autonomous driving module(s) 190 can cause the vehicle to accelerate (e.g., by increasing the supply of fuel provided to the engine), decelerate (e.g., by decreasing the supply of fuel to the engine and/or by applying brakes) and/or change direction (e.g., by turning the front two wheels).

The various elements of the system 100 can be communicatively linked to one another or one or more other elements through one or more communication networks 195. As used herein, the term "communicatively linked" can include direct or indirect connections through a communication channel, bus, pathway or another component or system. A "communication network" means one or more components designed to transmit and/or receive information from one source to another. The data store(s) 120 and/or one or more other elements of the system 100 can include and/or execute suitable communication software, which enables the various elements to communicate with each other through the communication network and perform the functions disclosed herein.

The one or more communication networks 195 can be implemented as, or include, without limitation, a wide area network (WAN), a local area network (LAN), the Public Switched Telephone Network (PSTN), a wireless network, a mobile network, a Virtual Private Network (VPN), the Internet, a hardwired communication bus, and/or one or more intranets. The communication network 195 further can be implemented as or include one or more wireless networks, whether short range (e.g., a local wireless network built using a Bluetooth or one of the IEEE 802 wireless communication protocols, e.g., 802.11a/b/g/i, 802.15, 802.16, 802.20, Wi-Fi Protected Access (WPA), or WPA2) or long range (e.g., a mobile, cellular, and/or satellite-based wireless network; GSM, TDMA, CDMA, WCDMA networks or the like). The communication network can include wired communication links and/or wireless communication links. The communication network can include any combination of the above networks and/or other types of networks.

Figure 2A:
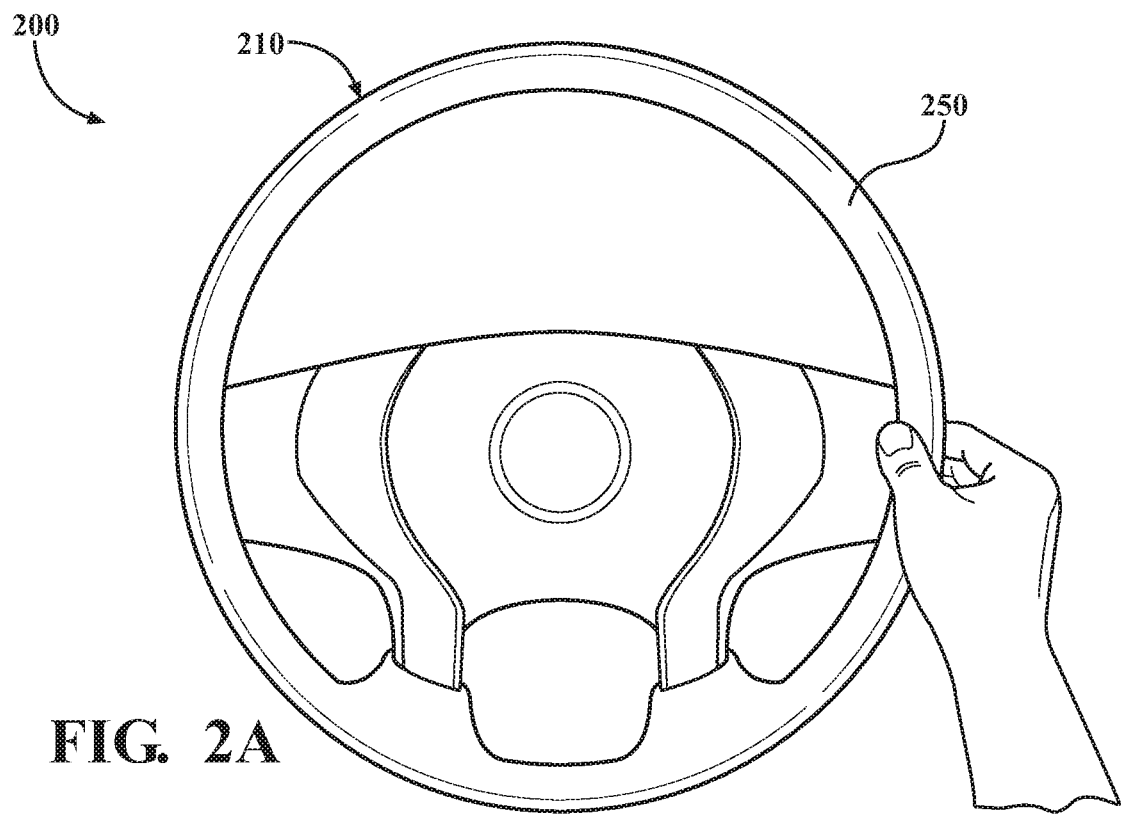
FIG. 2A shows an example of a steering wheel with a dynamic button in a non-activated mode.
Figure 2B:
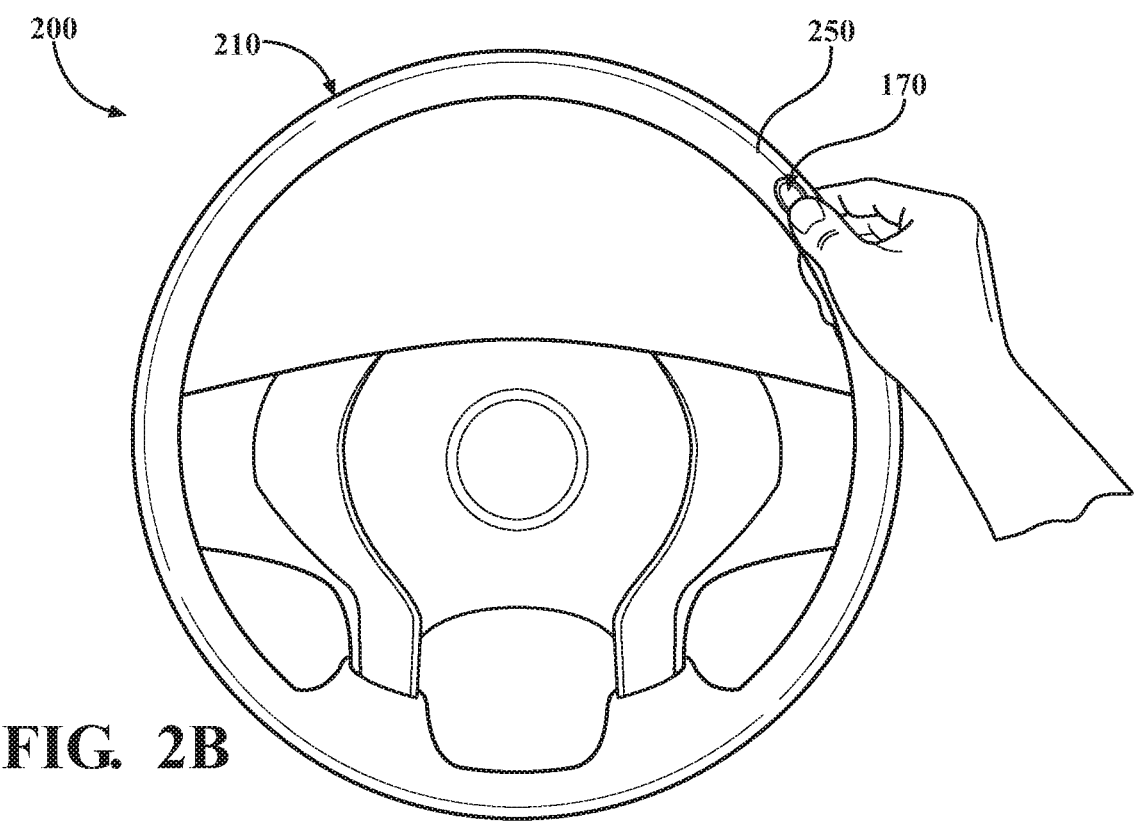
FIG. 2B shows an example of the steering wheel with the dynamic button in an activated mode.

Referring to FIGS. 2A-2B, one example of an implementation of the dynamic button 170 in a vehicle 200 is shown. In this example, the dynamic button 170 can be implemented in connection with a steering wheel 210 of the vehicle 200. FIG. 2A shows an example of the dynamic button 170 in a non-activated mode. In the non-activated mode, a deformable region 250 can appear to be substantially flat, and the dynamic button 170 is substantially not detectable by at least a user's sense of sight and/or touch.

FIG. 2B shows an example of the steering wheel with the dynamic button in an activated mode. In the activated mode, the region becomes visible and the user can find it by tactile or visual inspection of the steering wheel. When the dynamic button 170 is touched by a user, user biomonitoring can begin. The dynamic button 170 can be switched between the activated mode and the non-activated mode by the dynamic button module(s) 180.

While only one dynamic button 170 and one deformable region 250 is shown in FIG. 2B, it will be appreciated that there can be other dynamic buttons 170 and/or deformable regions 250 located on the steering wheel 210. It should be noted that the entire steering wheel 210 or one or more portions thereof can be configured to deform to define a dynamic button 170.

Further, the dynamic button 170 is shown as being located in the deformable region 250 on the steering wheel 210 in FIG. 2B, but it will be appreciated that the dynamic button 170 can be provided in other locations of the steering wheel 210 and/or on other components of the vehicle 200, such as on an arm rest, instrument panel, console, door, and/or gear shift. It should be noted that, when the steering wheel 210 or other vehicle component is configured to provide a plurality of dynamic buttons 170, the dynamic buttons 170 can be provided in non-overlapping locations. However, in other arrangements, a plurality of dynamic buttons 170 can be provided in locations that at least partially overlap, though such dynamic buttons 170 would not be activated that the same time.

Figure 6:
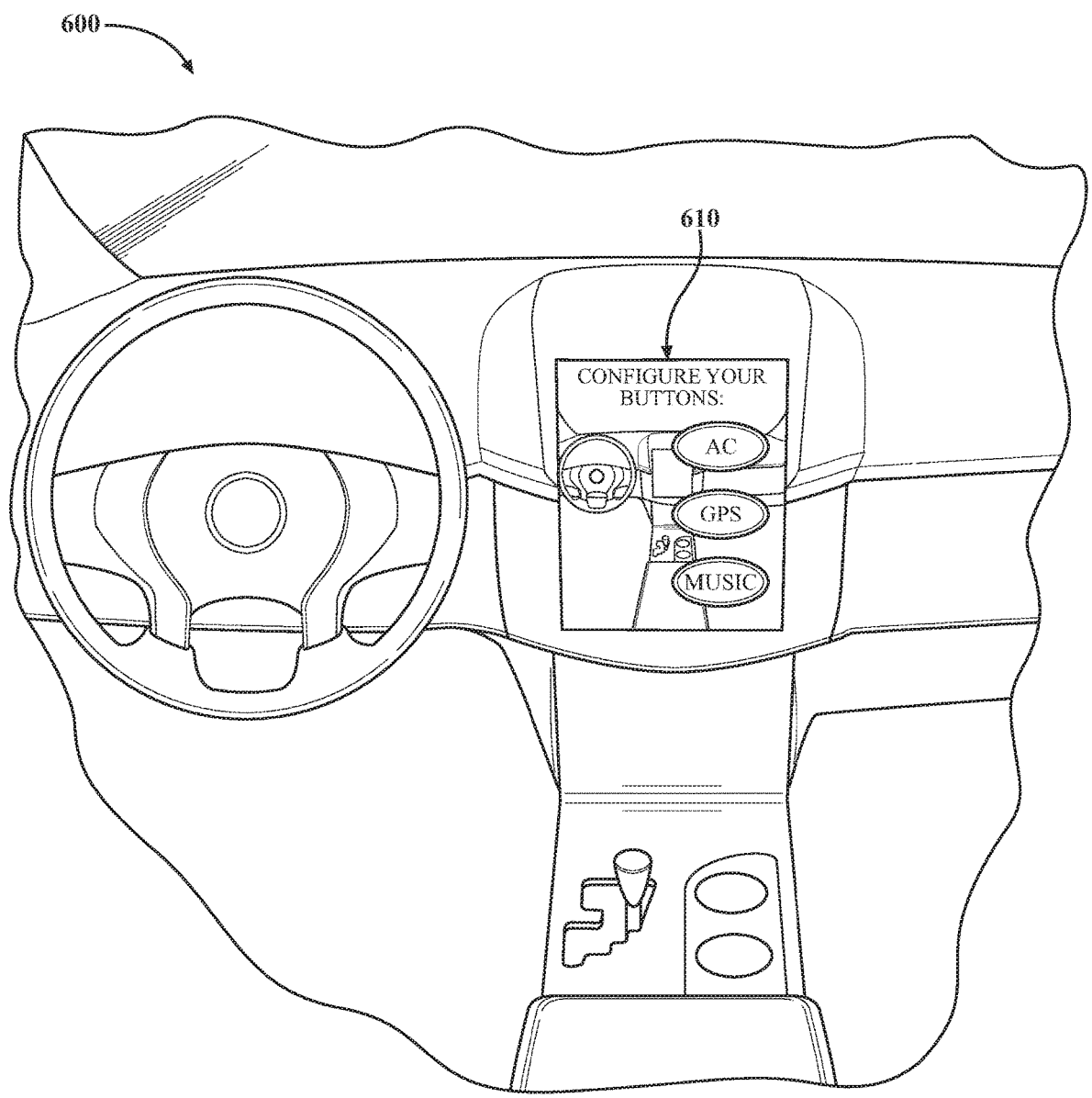
FIG. 6 shows a portion of a vehicle configured to allow a user to customize a dynamic button.

The dynamic button 170 can be user configurable. For instance, the size, shape, and/or location of the dynamic button 170 can be configured by a user. FIG. 6 shows a portion of a vehicle 600 configured to allow a user to customize a dynamic button. The vehicle can include a display 610, which can be a touchscreen display. The display 610 can present representation of the car's interior. By performing actions, such as tap and hold to drag buttons, the user can drag any dynamic buttons presented on the display 610 and place it in any region of the representation of the car's cockpit that is also being displayed in the touchscreen. By doing so, the real cockpit interface will reconfigure itself to display the dynamic button(s) 170 in the location(s) where the user set them. Likewise, the user can use simple commands such as tap to select a button and pinch/expand with two fingers to change the button size. Once the dynamic button 170 is selected on the display 610, the shape of the dynamic button 170 can also be controlled by a user. The user can select different designs for the dynamic button 170.

The dynamic button 170 can be formed in various suitable way. One particular example is shown in FIGS. 3A-3B, which shown a dynamically deformable surface 300. The dynamic button 170 can be formed by deformations in the dynamically deformable surface 300.

The dynamically deformable surface 300 can include one or more portions. For instance, the dynamically deformable surface 300 can include a first portion 310, a second portion 320, a third portion 330, and a fourth portion 340. In some arrangements, one or more of the first portion 310, the second portion 320, the third portion 330, and the fourth portion 340 can be a layer. Each of these portions 310, 320, 330, 340 will be described in turn below.

In one or more arrangements, the first portion 310 can include the biosensor(s) 132. The biosensors 132 can use biosensing technologies, now known or later developed, to enable the deformable surface 300 to perform measurements on a vehicle occupant (e.g., the driver). The first portion 310 can be a substantially continuous arrangement of the biosensors 132. In other arrangements, the first portion 310 may not be a continuous arrangement. Indeed, the first portion 310 can be defined by the location of each of the biosensors 132. Thus, the first portion 310 can include a plurality of discrete portions.

The second portion 320 can include a deformable material. The second portion 320 can be made of a flexible or compliant material. For instance, the second portion 320 can be made of liquid crystal elastomer (LCE). However, it will be appreciated that the second portion 320 can be made of any suitable material that can be deformed from an initial condition in response to a stimulus, and it can substantially return to the initial state when the stimulus is discontinued. The second portion 320 can be responsive to various stimuli, such as temperature, light, voltage, fluidic actuation, or any combination thereof.

The biosensor(s) 132 and the second portion 320 can be arranged in various ways. In one or more arrangements, the biosensor(s) 132 can be located on a surface of the second portion 320. In one or more arrangements, the biosensors 132 can be embedded at least partially within the second portion 320. In one or more arrangements, the biosensors 132 can be substantially flush with the second portion 320. In one or more arrangements, the first portion 310 can be an outermost portion of the dynamically deformable surface 300. "Outermost portion" means the portion that is located closest to the vehicle occupant (e.g., the driver) relative to the other portions. In some arrangements, the second portion 320 can at least partially define the outermost portion of the dynamically deformable surface 300.

The third portion 330 can include a plurality of actuators 335. The actuators 335 can be configured to, when activated, provide the stimulus to cause a deformation of a portion of the second portion 320. Thus, the shape of the second portion 320 and the deformable surface 300 can be controlled by actuation of one or more of the actuators 335 of the third portion 330.

The actuators 335 can be arranged in any suitable manner. In one or more arrangements, the third portion 330 can include an array or matrix of the actuators 335. The actuators 335 can be configured for individual operation. Thus, the shape, size, and/or location of the deformation of the second portion 320 can be controlled. It will be appreciated that the dynamic buttons 170 can be defined by the deformations of the second portion 320. Alternatively or in addition, the actuators 335 can be configured to cause changes in the texture, stiffness, and/or color of the second portion 320.

The actuators 335 can be configured to provide a stimulus to cause changes in size, shape, configuration, stiffness, texture and/or color of the second portion 320. In one or more arrangements, the actuators 335 can be a plurality of light sources, which can provide light energy as a stimulus to the second portion 320. Examples of other stimuli can be provided by the actuators 335 can include voltage or temperature. In some arrangements, the actuators 335 can be compliant mechanisms, solenoids, or soft-bodied actuators.

The fourth portion 340 can include one or more touch sensors. The fourth portion 340 can be configured to detect the touching of the deformable surface 300 by a portion of the body of a human being. For instance, the touch sensors can be pressure, capacitive, and/or piezoelectric sensors. The touch sensors can be configured to detect human touch and/or a pressing of the deformable surface. In one or more arrangements, the fourth portion 340 can be defined by a single continuous touch sensor. In one or more arrangements, the fourth portion 340 can be defined by a plurality of touch sensors. While the fourth portion 340 is shown as being the innermost portion of the dynamically deformable surface 300, it will be appreciated that the fourth portion 340 is not limited to such a location. The fourth portion 340 can be provided in any suitable location relative to the other portions.

FIG. 3A shows an example of the dynamically deformable surface 300 in a non-activated mode. In such case, the deformable surface 300 can be substantially flat or in some other initial configuration. FIG. 3B shows an example of the deformable surface 300 in an activated mode. In the activated mode, a subset of the actuators 335 of the third portion 330 can be activated. In this example, the actuators 335 can be light sources. The light energy emitted by the actuators 335 can cause corresponding areas of the second portion 320 to deform, as is shown in FIG. 3B. For instance, a portion of the second portion 320 can bulge outward, thereby forming the dynamic button 170. In such case, the dynamic button 170 can be a protrusion from the dynamically deformable surface 300. In some arrangements, the second portion 320 can be configured to depress inwardly in response to the stimulus. In such arrangements, the dynamic button 170 can be a recess formed in the dynamically deformable surface 300.

It will be appreciated that the above description of the deformable surface is merely one example. Various other suitable arrangements are possible. For instance, the portions can be arranged in any suitable manner, including in ways that are different than that shown in FIGS. 3A-3B. In some arrangements, two or more of the portions 310, 320, 330, 340 may be combined into one portion. Further, the deformable surface 300 may not include one or more of the portions described above. As an example, in some arrangements, the second portion 320 may deform in response to the temperature of a person's skin. In such case, there may not need for the third portion 330. As an alternative, the deformable surface 300 may still include the third portion 330, but it can provide a function other than providing a stimulus to cause a deformation of the second portion 320. Still further, the deformable surface 300 may include additional or alternative portions to those described above.

In some arrangements, the dynamically deformable surface 300 can be configured to provide information to a user. For instance, the stiffness of a region of the dynamically deformable surface 300 can be activated to have a surface texture and/or stiffness that is different from the surface texture and/or stiffness of the rest of the dynamically deformable surface 300. Such regions can draw a user's attention to the dynamic button 170, or it can indicate to a user that the region is one that could become a dynamic button 170.

In some arrangements, the dynamically deformable surface 300 can be configured to become transparent in response to a stimulus (e.g., heat and/or light). Such transparency can draw a user's attention to the area. In some arrangements, the transparent area can be illuminated in a particular color by light sources in the third portion 330. By illuminating the region, it can further draw a user's attention to the area and/or indicate that some activity is to be performed in the illuminated location. In some arrangements, the dynamic button 170 can be illuminated in a particular color to indicate when biosensing is occurring. It should be noted that the third portion 330 can include a first set of one or more light sources that can provide a activation stimulus to the second portion 320, and it can further include a second set of one or more light sources that serve as light sources to illuminate a portion of the dynamic button(s) 170 and/or a portion of the second portion 320 without stimulating the second portion 320. These light sources can have different light energy characteristics (e.g., wavelength), which can cause their different effect to the second portion 320.

Now that the various potential systems, devices, elements and/or components of the system 100 have been described, various methods of using the system 100 will now be described. Various possible steps of such methods will now be described. The methods described may be applicable to the arrangements described above, but it is understood that the methods can be carried out with other suitable systems and arrangements. Moreover, the methods may include other steps that are not shown here, and in fact, the methods are not limited to including every step shown. The blocks that are illustrated here as part of the methods are not limited to the particular chronological order. Indeed, some of the blocks may be performed in a different order than what is shown and/or at least some of the blocks shown can occur simultaneously.

Figure 4:
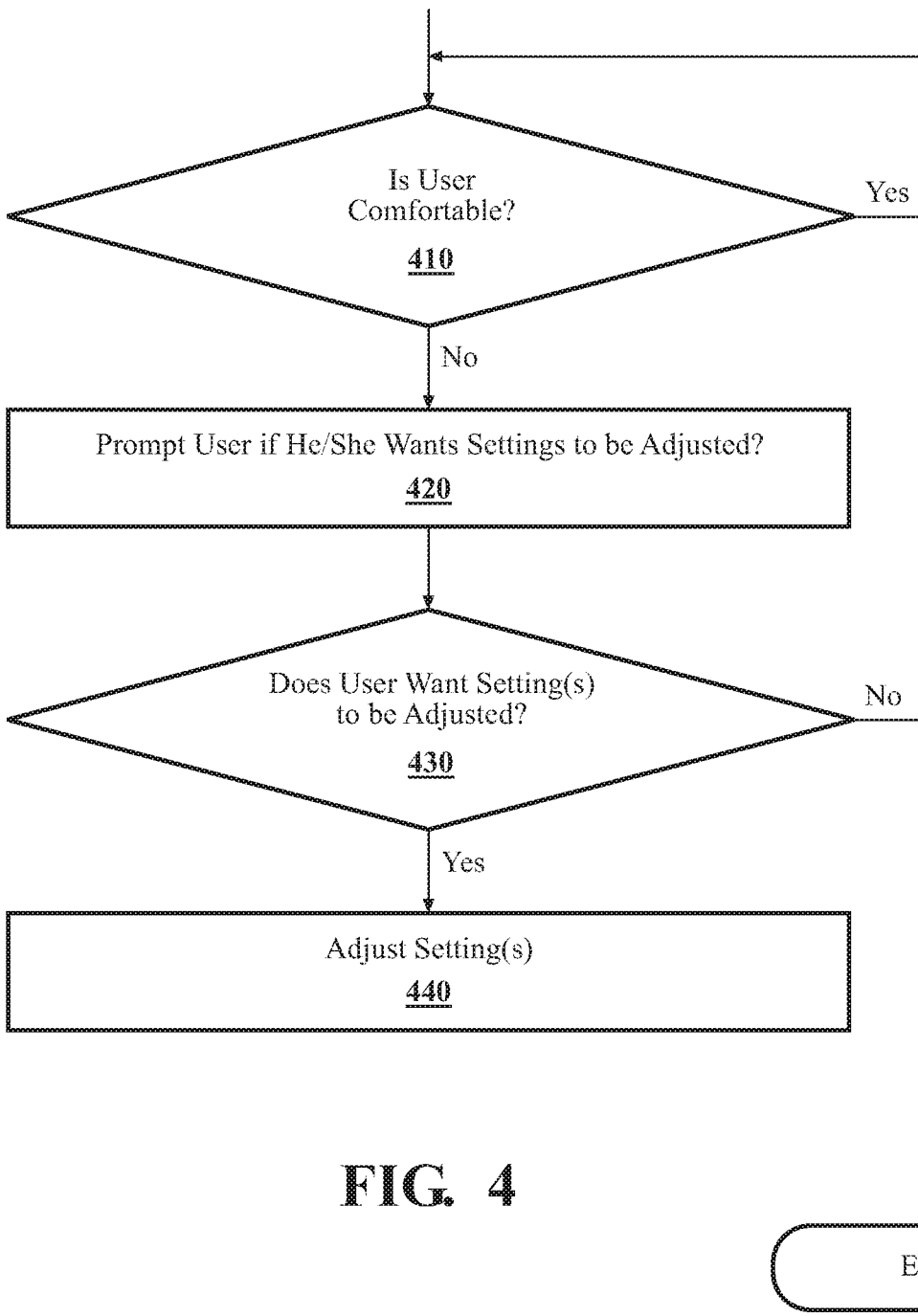
FIG. 4 is an example of a method for detecting and/or adjusting user comfort.

Turning to FIG. 4, an example of a method 400 for detecting and/or adjusting user comfort. Depending on a user's comfort level, different actions can be taken. For the sake of discussion, the method 400 can begin with the dynamic button(s) 170 in an activated mode, such as is shown in FIG. 2B, and the user can be engaging the dynamic button(s) 170 with some portion of his or her body.

At block 410, it can be determined whether the user is comfortable. Such a determination can be made by the user comfort module(s) 182 and/or the processor(s) 110. For instance, the user comfort module(s) 182 and/or the processor(s) 110 can determine user comfort based at least in part on user biodata acquired by the biosensor(s) 132. In some instances, the determination can also be based on data acquired by the vehicle sensor(s) 134 or other sensor(s) 130. If the user is determined to be comfortable, the method 400 can end, return to block 410, or proceed to some other block. However, if it is determined that the user is not comfortable, then the method 400 can proceed to block 420.

At block 420, the user can be prompted as to whether he or she wants one or more vehicle settings to be adjusted. Such prompting can be performed by the vehicle settings control module(s) 184 and/or the processor(s) 110. More particularly, the vehicle settings control module(s) 184 and/or the processor(s) 110 can prompt the user via the output interface(s) 145. The prompting can be visual, such as on a display, or it can be audial, such as over one or more speakers. The prompt can inform the user of the vehicle setting and/or the proposed adjustment to the vehicle setting. For instance, the prompt can be in the form of a question: "Would you like to increase the cabin temperature?" The method 400 can proceed to block 430.

At block 430, it can be determined whether a user input has been received is response to the prompt. The user input can be received via the input interface(s) 140. The vehicle settings control module(s) 184 and/or the processor(s) 110 can analyze the user input to determine if it is indicative of the user wanting the adjust the vehicle setting(s) or if it is indicative of the user not wanted the vehicle setting(s) to be adjusted. Any suitable analysis, now known or later developed, can be performed on the user input. If it is determined that the user does not want the vehicle setting(s) to the adjusted, the method 400 can end, return to block 410, or proceed to some other block. However, if it is determined that the user wants the vehicle setting(s) to be adjusted, the method 400 can proceed to block 440.

At block 440, the vehicle setting(s) can be adjusted. The vehicle settings control module(s) 184 and/or the processor(s) 110 can cause the vehicle setting(s) to be adjusted. For instance, the vehicle settings control module(s) 184 and/or the processor(s) 110 can send control signals to the actuator(s) 150. After block 440, the method 400 can end. Alternatively, the method 400 can return to block 410 or some other block. The method 400 can be performed continuously, periodically, irregularly, randomly, or responsive to a condition, event, or input.

Figure 5:
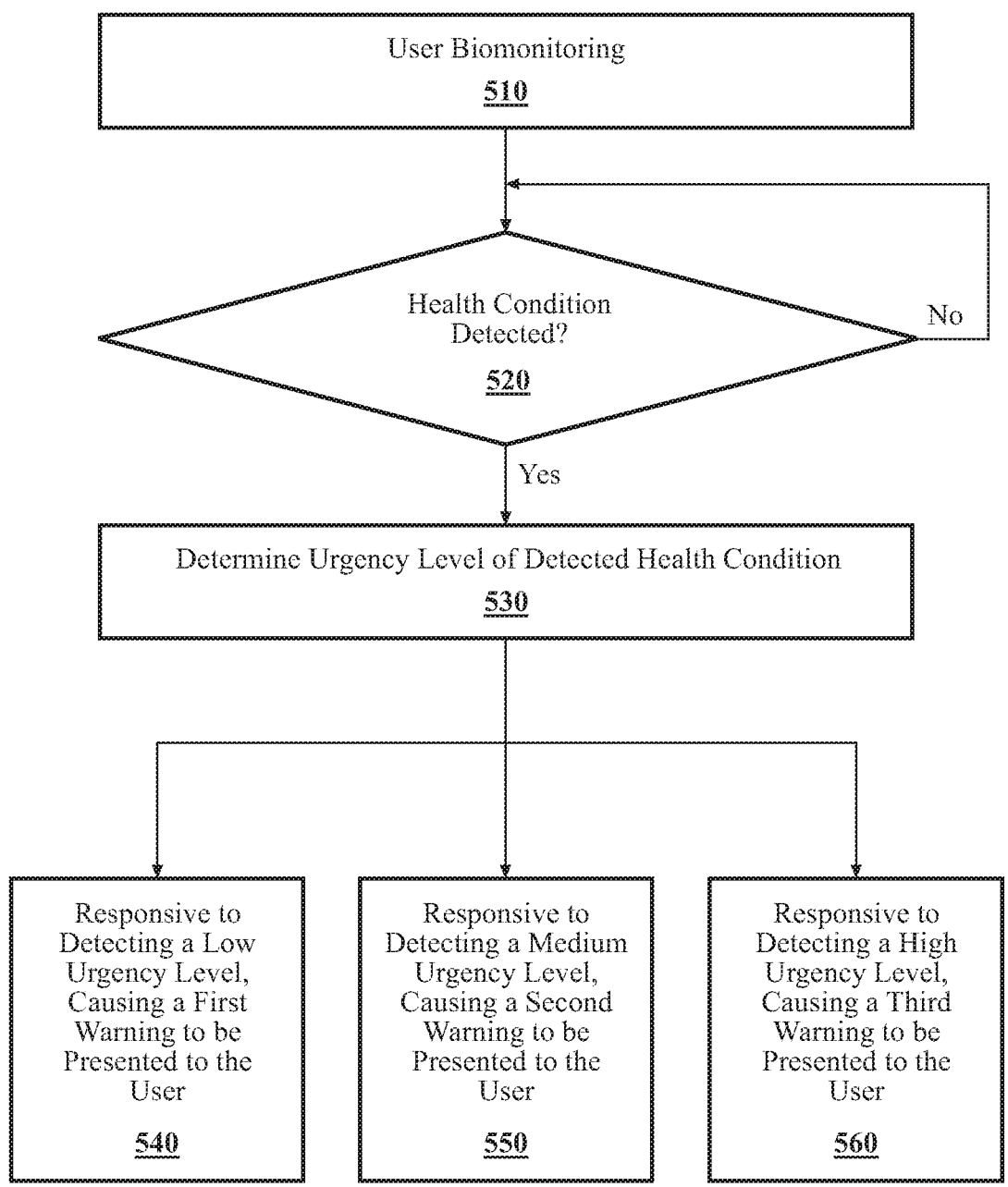
FIG. 5 is an example of a method for detecting and/or warning of a user health condition.

Turning to FIG. 5, an example of a method for detecting and/or warning of a user health condition is shown. Depending on the condition detected, different actions can be taken. For the sake of discussion, the method 500 can begin with the dynamic button(s) 170 in an activated mode, such as is shown in FIG. 2B.

At block 510, user biomonitoring can occur. Thus, user biodata can be acquired by the biosensor(s) 132 associated with the dynamic button(s) 170 as a user engages the dynamic button(s) 170 with a portion of his or her body. Acquired user biodata can be stored in the one or more data store(s) 120. The method 500 can proceed to block 520.

At block 520, the acquired user biodata can be analyzed to detect a health condition. Such analyzing can be performed using the user health module(s) and/or the processor(s) 110. The analyzing can also use health condition data, which can be located onboard the vehicle or in a remote source. The health data can include information about various health conditions, such as symptoms or biomarkers. The analyzing can use big data. If a health condition is not detected, the method 500 can end, return to block 510, or proceed to some other block. However, if a health condition is detected, then the method 500 can proceed to block 530.

At block 530, an urgency level of the detected health condition can be determined. Such a determination can be made by, for example, the user health module(s) 186 and/or the processor(s) 110. The determination can be made using information or data included in the data store(s) 120. The method 500 can proceed to block 540, block 550, or block 560, depending on the urgency level of the health condition detected. Each will be described in turn below.

At block 540, in response to detecting a low urgency level, a first warning can be caused to be presented to the user. Examples of low urgency level health conditions can include cold, sore throats, influenza, etc. For instance, the warning module(s) 188 and/or the processor(s) 110 can cause the first warning to be output on the output interface(s) 145. The first warning can be visual, audial, and/or haptic. The first warning can have any suitable content. As an example, the first warning can be "You may be developing symptoms of _____. We suggest that you rest. We can order useful remedies online or drive to the nearest pharmacy." If the user requests the vehicle to order useful remedies, then the vehicle can order such remedies. Alternatively or in addition, if the user requests the vehicle to the nearest pharmacy, then the vehicle can navigate the user and/or autonomously drive the vehicle to the pharmacy. For instance, the user may have medical provider or pharmacy contact information store in the data store(s) 120. Alternatively, the vehicle can acquire such information based on a present location of the vehicle.

At block 550, in response to detecting a medium urgency level, a second warning can be caused to be presented to the user. An example of a medium urgency level can include food poisoning. For instance, the warning module(s) 188 and/or the processor(s) 110 can a warning to be output on the output interface(s) 145. The second warning can be visual, audial, and/or haptic. The second warning can have any suitable content. As an example, the second warning can be "You may be developing symptoms of _____. Would you like to schedule a doctor's appointment?" If the user requests the vehicle to order schedule an appointment, then the vehicle can contact the appropriate doctor and schedule an appointment. For instance, the user may have medical provider contact information store in the data store(s) 120.

At block 560, in response to detecting a high urgency level, the vehicle can cause a third warning can be caused to be presented to the user. Examples of high urgency level health conditions can include heart attack or stroke. For instance, the warning module(s) 188 and/or the processor(s) 110 can cause the third warning to be output on the output interface(s) 145. The third warning can be visual, audial, and/or haptic. The first warning can have any suitable content. As an example, the second warning can be "We detected symptoms of _____. We can drive you to the nearest healthcare facility." If the user requests the vehicle to the nearest pharmacy, then the vehicle can navigate the user and/or autonomously drive the vehicle to the pharmacy. For instance, the user may have medical provide contact information store in the data store(s) 120. Or the vehicle can acquire based on a present location of the drive.

After block 540, block 550, or block 560, the method 500 can end. Alternatively, the method 500 can return to block 510 or some other block. The method 500 can be performed continuously, periodically, irregularly, randomly, or responsive to a condition, event, or input.

It will be appreciated that arrangements described herein can provide numerous benefits, including one or more of the benefits mentioned herein. For example, arrangements described herein can enable a vehicle's interior can produce regions to act as buttons on demand, depending on the needs and application. By doing so, buttons and other input forms can appear and disappear depending on context. Arrangements described herein can allow for a cleaner cockpit interface. Arrangements described herein can greatly expand the possibilities of where the buttons can be located at and how many things can be controlled by the driver using physical interfaces. Arrangements described herein can enable a vehicle to operate as a health-monitoring system or a comfort-monitoring system without the risk of creating an interface that is visually overwhelming.

It should be noted that the vehicle can be any type of vehicle. For instance, in one or more arrangements, the vehicle can be an autonomous vehicle. As used herein, "autonomous vehicle" means a vehicle that configured to operate in an autonomous operational mode. "Autonomous operational mode" means that one or more computing systems are used to navigate and/or maneuver the vehicle along a travel route with minimal or no input from a human driver. In one or more arrangements, the vehicle can be highly automated or completely automated.

The vehicle can have one or more semi-autonomous operational modes in which a portion of the navigation and/or maneuvering of the vehicle along a travel route is performed by one or more computing systems, and a portion of the navigation and/or maneuvering of the vehicle along a travel route is performed by a human driver. The vehicle can have a manual operational mode in which all of or a majority of the navigation and/or maneuvering of the vehicle is performed by a human driver. In one or more arrangements, the vehicle can be a conventional vehicle that is configured to operate in only a manual mode.

The vehicle can be configured to be switched between the various operational modes, including between any of the above-described operational modes. Such switching can be implemented in any suitable manner, now known or later developed. The switching can be performed automatically, selectively, or it can be done responsive to receiving a manual input or request.

The flowcharts and block diagrams in the figures illustrate the architecture, functionality, and operation of possible implementations of systems, methods and computer program products according to various embodiments. In this regard, each block in the flowcharts or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved.

The systems, components and/or processes described above can be realized in hardware or a combination of hardware and software and can be realized in a centralized fashion in one processing system or in a distributed fashion where different elements are spread across several interconnected processing systems. Any kind of processing system or other apparatus adapted for carrying out the methods described herein is suited. A typical combination of hardware and software can be a processing system with computer-usable program code that, when being loaded and executed, controls the processing system such that it carries out the methods described herein. The systems, components and/or processes also can be embedded in a computer-readable storage, such as a computer program product or other data programs storage device, readable by a machine, tangibly embodying a program of instructions executable by the machine to perform methods and processes described herein. These elements also can be embedded in an application product which comprises all the features enabling the implementation of the methods described herein and, which when loaded in a processing system, is able to carry out these methods.

Furthermore, arrangements described herein may take the form of a computer program product embodied in one or more computer-readable media having computer-readable program code embodied, e.g., stored, thereon. Any combination of one or more computer-readable media may be utilized. The computer-readable medium may be a computer-readable signal medium or a computer-readable storage medium. The phrase "computer-readable storage medium" means a non-transitory storage medium. A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk drive (HDD), a solid state drive (SSD), a random access memory (RAM), a read-only memory (ROM), an erasable programmable read-only memory (EPROM or Flash memory), an optical fiber, a portable compact disc read-only memory (CD-ROM), a digital versatile disc (DVD), an optical storage device, a magnetic storage device, or any suitable combination of the foregoing. In the context of this document, a computer-readable storage medium may be any tangible medium that can contain, or store a program for use by or in connection with an instruction execution system, apparatus, or device.

The terms "a" and "an," as used herein, are defined as one or more than one. The term "plurality," as used herein, is defined as two or more than two. The term "another," as used herein, is defined as at least a second or more. The terms "including" and/or "having," as used herein, are defined as comprising (i.e. open language). The term "or" is intended to mean an inclusive "or" rather than an exclusive "or." The phrase "at least one of . . . and . . . ." as used herein refers to and encompasses any and all possible combinations of one or more of the associated listed items. As an example, the phrase "at least one of A, B and C" includes A only, B only, C only, or any combination thereof (e.g. AB, AC, BC or ABC). As used herein, the term "substantially" or "about" includes exactly the term it modifies and slight variations therefrom. Thus, the term "substantially parallel" means exactly parallel and slight variations therefrom. "Slight variations therefrom" can include within 15 degrees/percent/units or less, within 14 degrees/percent/units or less, within 13 degrees/percent/units or less, within 12 degrees/percent/units or less, within 11 degrees/percent/units or less, within 10 degrees/percent/units or less, within 9 degrees/percent/units or less, within 8 degrees/percent/units or less, within 7 degrees/percent/units or less, within 6 degrees/percent/units or less, within 5 degrees/percent/units or less, within 4 degrees/percent/units or less, within 3 degrees/percent/units or less, within 2 degrees/percent/units or less, or within 1 degree/percent/unit or less. In some instances, "substantially" can include being within normal manufacturing tolerances.

Aspects herein can be embodied in other forms without departing from the spirit or essential attributes thereof. Accordingly, reference should be made to the following claims, rather than to the foregoing specification, as indicating the scope of the invention.

What is claimed is:

1. A system comprising:
   a vehicle component;
   a dynamically deformable surface provided on the vehicle component, the dynamically deformable surface including a compliant portion and a plurality of actuators operatively positioned relative to the compliant portion, the compliant portion being deformable responsive to a stimulus produced by the actuators to form a dynamic button;
   one or more biosensors, the one or more biosensors being a part of the dynamically deformable surface; and
   one or more processors operatively connected to the dynamically deformable surface and to the one or more biosensors, the one or more processors being configured to:
      cause the dynamically deformable surface to deform to form the dynamic button; and
      responsive to the dynamic button being engaged by a body portion of a user, acquire, using the one or more biosensors, user biodata.

2. The system of claim 1, wherein the one or more processors are further configured to:
   determine based on at least user biodata whether the user is comfortable.

3. The system of claim 2, wherein determine based on at least user biodata whether the user is comfortable includes determine based on at least user biodata and vehicle data whether the user is comfortable.

4. The system of claim 2, wherein the one or more processors are further configured to:
- responsive to determining that the user is not comfortable, determine an adjustment to a vehicle setting to increase the comfort of the user; and
- cause a prompt to be presented to the user as to whether the user wants the vehicle setting to be adjusted.

5. The system of claim 4, wherein the one or more processors are further configured to:
- responsive to receiving a user input indicating that the user wants the vehicle setting to be adjusted, causing the vehicle setting to be adjusted.

6. The system of claim 1, wherein the one or more processors are further configured to analyze the user biodata to detect whether the user has a health condition.

7. The system of claim 6, wherein the one or more processors are further configured to:
- responsive to detecting a health condition, determine an urgency level of the detected health condition.

8. The system of claim 7, wherein the one or more processors are further configured to:
- cause a warning to be presented to the user based on at least one of the health condition or the determined urgency level of the detected health condition.

9. The system of claim 1, wherein at least one of a size, shape, stiffness, and location of the dynamic button is user configurable.

10. The system of claim 1, wherein the actuators are configured to output at least one of light energy, voltage, and thermal energy, and wherein the compliant portion is deformable responsive to at least one of light energy, voltage, thermal energy, and fluidic actuation.

11. The system of claim 1, wherein the one or more biosensors are location on or at least partially within the compliant portion.

12. The system of claim 1, wherein the dynamically deformable surface further includes one or more touch sensors, whereby the touch sensors are configured to detect a touching of the dynamically deformable surface by a portion of a human body.

13. The system of claim 1, wherein, when activated, the dynamic button is a protrusion.

14. A method comprising:
- causing a dynamically deformable surface to deform to form a dynamic button, the dynamically deformable surface being located on a vehicle component, the dynamically deformable surface including one or more biosensors; and
- responsive to the dynamic button being engaged by a body portion of a user, acquiring, using the one or more biosensors, user biodata,
- the dynamically deformable surface including a compliant portion and a plurality of actuators operatively positioned relative to the compliant portion, the compliant portion being deformable responsive to a stimulus produced by the actuators.

15. The method of claim 14, further including:
determining based on at least user biodata whether the user is comfortable.

16. The method of claim 14, further including:
- responsive to determining that the user is not comfortable, determining an adjustment to a vehicle setting to increase user comfort;
- causing a prompt to be presented to the user as to whether the user wants the vehicle setting to be adjusted; and
- responsive to receiving a user input indicating that the user wants the vehicle setting to be adjusted, causing the vehicle setting to be adjusted.

17. The method of claim 14, further including:
analyzing the user biodata to detect whether the user has a health condition.

18. The method of claim 17, further including:
- responsive to detecting a health condition, determine an urgency level of the detected health condition; and
- cause a warning to be presented to the user, wherein the warning is based on at least one of the health condition and the determined urgency level of the detected health condition.

* * * * *